(12) United States Patent
Liu et al.

(10) Patent No.: US 12,396,068 B2
(45) Date of Patent: Aug. 19, 2025

(54) VAPOUR GENERATING DEVICE (71) Applicant: JT International S.A., Geneva (CH)

(72) Inventors: Pingkun Liu, Guangdong (CN); Yongbao Yuan, Guangdong (CN); Min Xu, Weybridge (GB); Damian Dickson, Ballymena (GB); Gordon Montgomery, Ballymena (GB)

(73) Assignee: JT International S.A. (CH)

( * ) Notice: Subject to any disclaimer, the term of this patent is extended or adjusted under 35 U.S.C. 154(b) by 1196 days.

(21) Appl. No.: 16/972,394

(22) PCT Filed: Jun. 20, 2019

(86) PCT No.: PCT/EP2019/066344
§ 371 (c)(1),
(2) Date: Dec. 4, 2020

(87) PCT Pub. No.: WO2019/243494
PCT Pub. Date: Dec. 26, 2019

(65) Prior Publication Data
US 2021/0227888 A1    Jul. 29, 2021

(30) Foreign Application Priority Data

Jun. 20, 2018 (EP) .................................. 18178688

(51) Int. Cl.
*A24F 13/00* (2006.01)
*A24F 40/20* (2020.01)
(Continued)

(52) U.S. Cl.
CPC ............... *H05B 3/42* (2013.01); *A24F 40/20* (2020.01); *A24F 40/46* (2020.01); *A24F 40/485* (2020.01); *A24F 40/50* (2020.01); *A24F 40/10* (2020.01)

(58) Field of Classification Search
CPC .................................................... A24F 48/00
(Continued)

(56) References Cited

U.S. PATENT DOCUMENTS 10,299,514 B2 * 5/2019 Bilat ....................... H05B 3/44
10,561,803 B2 * 2/2020 Liu ........................ A24F 40/40
(Continued)

FOREIGN PATENT DOCUMENTS

CN    203873018 U    10/2014
CN    107536113 A    1/2018
(Continued)

OTHER PUBLICATIONS

International Search Report for Application No. PCT/EP2019/066344, mailed Dec. 8, 2019, 4 pages.
(Continued)

*Primary Examiner* — Phuong K Dinh
(74) *Attorney, Agent, or Firm* — Lerner David LLP (57) ABSTRACT

A vapour generating device is arranged to receive solid vapour generating material. The vapour generating device includes a vapour generating chamber which is arranged to contain the solid vapour generating material and a closure for the vapour generating chamber. The closure is arranged to define a first passageway between the exterior of the vapour generating device and the vapour generating chamber when the closure is in a closed position, such that the first passageway allows air to enter the vapour generating chamber.

20 Claims, 4 Drawing Sheets

(51) Int. Cl.
    *A24F 40/46*     (2020.01)
    *A24F 40/485*     (2020.01)
    *A24F 40/50*     (2020.01)
    *H05B 3/42*     (2006.01)
    *A24F 40/10*     (2020.01)

(58) Field of Classification Search
    USPC .................................................. 131/328–329
    See application file for complete search history.

(56) References Cited

U.S. PATENT DOCUMENTS

| | | | |
|---|---|---|---|
| 2017/0156403 | A1 | 6/2017 | Gill et al. |
| 2018/0020733 | A1 | 1/2018 | Jochnowitz |
| 2018/0271154 | A1 | 9/2018 | Leadley et al. |

FOREIGN PATENT DOCUMENTS

| | | | |
|---|---|---|---|
| CN | 107752130 | A | 3/2018 |
| CN | 207252788 | U | 4/2018 |
| GB | 2527597 | A | 12/2015 |
| JP | 2017526381 | A | 9/2017 |
| JP | 2018508211 | A | 3/2018 |
| KR | 20170110566 | A | 10/2017 |
| KR | 20170121162 | A | 11/2017 |
| KR | 20180043341 | A | 4/2018 |
| WO | 2013034456 | A1 | 3/2013 |
| WO | 2013102611 | A2 | 7/2013 |
| WO | 2013131764 | A1 | 9/2013 |
| WO | 2015177044 | A1 | 11/2015 |
| WO | WO 2016/135271 | * | 1/2016 |
| WO | 2016033734 | A1 | 3/2016 |
| WO | 2016107762 | A1 | 7/2016 |
| WO | 2016135271 | A1 | 9/2016 |
| WO | 2017051150 | A1 | 3/2017 |
| WO | 2017167932 | A1 | 10/2017 |
| WO | 2017194751 | A1 | 11/2017 |
| WO | 2017207419 | A1 | 12/2017 |
| WO | 2017218982 | A1 | 12/2017 |
| WO | 2017220274 | A1 | 12/2017 |
| WO | 2018019533 | A1 | 2/2018 |

OTHER PUBLICATIONS

Notice of opposition to a European patent for Application No. 19730847.1 dated Dec. 9, 2024, pp. 1-6.

* cited by examiner

VAPOUR GENERATING DEVICE

CROSS-REFERENCE TO RELATED APPLICATIONS

The present application is a national phase entry under 35 U.S.C. § 371 of International Application No. PCT/EP2019/066344, filed Jun. 20, 2019, published in English, which claims priority to European Application No. 18178688.0 filed Jun. 20, 2018, the disclosures of which are incorporated herein by reference.

FIELD OF THE INVENTION

The present invention relates to a vapour generating device with a passageway for allowing air to be drawn into the device.

BACKGROUND

Devices which heat, rather than burn, a substance to produce a vapour for inhalation have become popular with consumers in recent years.

Many hand-held vapour generating devices comprise a chamber surrounded by a heating mechanism and connected to a mouthpiece. A vapour-generating substance is placed inside the chamber and the heating mechanism causes a vapour to be generated which can be inhaled by the user through the mouthpiece.

Many hand-held vapour generating devices have fairly complex structures which require the user to partially dismantle the vapour generating device in order to insert the vapour generating material into the chamber. The complex nature of current devices may increase the chance that the user does not put the device back together properly after inserting the substance into the chamber.

Requiring the user to partially dismantle the device increases the chance of the user coming into contact with internal part of the device which may be dangerous, for example the heating element which may still be hot.

If the vapour generating device is a hand-held device, it is important to ensure that the user does not end up blocking air inlets while they are holding the device as this will prevent sufficient amounts of air from being drawn into the device. Furthermore, if air that is drawn into the chamber is not circulated properly around the chamber, the quality of the vapour generated from the vapour generating material will suffer.

It would be desirable to provide a vapour generating device which provides improved air flow around the chamber whilst keeping the structure of the device simple and safe to use. The present invention therefore seeks to overcome at least some of the above problems.

SUMMARY OF THE INVENTION

According to an aspect of the present invention there is provided a vapour generating device arranged to receive solid vapour generating material, the device comprising a vapour generating chamber arranged to contain the solid vapour generating material, a closure arranged to seal the vapour generating chamber, and a first passageway arranged between the exterior of the vapour generating device and the vapour generating chamber when the closure is in a closed position, such that the passageway allows air to enter the vapour generating chamber, wherein either: the vapour generating chamber comprises a first wall and the first passageway is arranged to extend through the first wall and surround at least part of the first wall; or the vapour generating chamber comprises a side wall arranged to define the first passageway between the closure and the side wall; or the vapour generating chamber comprises a side wall and the first passageway is arranged to surround the vapour generating chamber at a base of the side wall.

The device therefore provides a simple structure which effectively draws air into the device and circulates the air around the vapour generating chamber. This insures good air circulation whilst also providing a simple mechanism for a user to insert vapour generating material for vaporisation. It also enables provision of a vapour generating device in which the user is protected from accidental contact with the vapour generating chamber. Furthermore, the configuration of the passageway in the device ensures that the user will not cover the passageway when holding the device.

As mentioned, the closure is arranged to seal the vapour generating chamber. In this context, "seal" means that the closure is arranged to prevent a user from accessing the heating chamber and to prevent the vapour generating material from getting into or out of the vapour generating chamber, once the chamber has been sealed. Thus, the closure acts like a door and is therefore arranged to close the vapour generating chamber. The term "seal" does not mean that the closure prevents air from entering the heating chamber. Thus the closure is not a hermetic seal.

The first passageway may be in any suitable shape which allows air to be drawn into the vapour generating chamber For example, in some embodiments the first passageway may comprise a plurality of small substantially circular openings or a plurality of substantially polygonal shaped openings such as rectangles. The plurality of openings may be arranged in an annular arrangement. The plurality of openings may be substantially evenly spaced apart from each other. In other embodiments the opening may be a single opening having an annular shape.

The closure may be arranged to define the first passageway of the vapour generating device when the closure is in a closed position.

The first passageway may surround at least part of the total area of the first wall of the closure. Preferably the first passageway surrounds at least 50% of the total area of the first wall. Advantageously, this may allow the air that is drawn into the device to flow uniformly across the vapour generating chamber helping to effectively create vapour from the vapour generating material.

In this context, the area that is surrounded by the opening may be considered to be an area defined by a virtual rope or perimeter where the path of the virtual rope or perimeter is defined by the position of the openings. The openings may be thought of as posts, such as fence posts. A virtual rope may then be wrapped around the posts defining a perimeter. The shape of the perimeter may depend on the configuration of the openings. For example, a large number of openings in an annular arrangement would form a substantially circular path. In other examples, a small number of openings would form a polygon for example three openings would form a triangle. The area surrounded by the path traced by the virtual rope or perimeter is the area that is surrounded by the openings.

The first passageway may comprise a plurality of gaps between the closure and the side wall. Thus the passageway may be formed by two grooves when the closure is in an open position and not sealing the vapour generating chamber. In other words, the gaps forming the first passageway may comprise a plurality of grooves, for example two grooves, located within the side wall of the vapour generating chamber. When the closure is in a closed position, sealing the vapour generating chamber, the closure may cover the grooves in the side wall so that gaps are formed, these gaps forming the first passageway. If the air flow passage is formed by two grooves or a groove and a flat surface, a user can access the inside of the first passageway when the closure is in the open position. Advantageously, the user can easily clean the inside of the first passageway. The device is therefore easy to maintain.

In some embodiments, the first passageway may be arranged such that air that enters the vapour generating chamber is directed towards a central axis of the vapour generating chamber. This ensures that air is uniformly circulated around the vapour generating chamber. In other embodiments, it is not always necessary that all the air that enters the vapour generating chamber is directed towards the central axis. Thus, in some embodiments at least part of the air flow is directed towards the central axis of the vapour generating chamber and at least part of the air flow is directed parallel to the central axis of the vapour generating chamber. Advantageously, these airflow paths may also improve the uniformly circulated airflow in the vapour generating chamber.

The vapour generating chamber may comprise a second passageway substantially opposite the first passageway, defined within a wall of the vapour generating chamber. The second passageway may be between the interior of the vapour generating chamber and an air outlet. Thus, the second passageway may be in fluid communication with the air outlet. The air outlet may be a mouthpiece. The second passageway may allow the vapour to exit the vapour generating chamber. This ensures that air is uniformly circulated around the vapour generating chamber.

The vapour generating chamber may comprise a second wall substantially opposite the first wall and the second passageway may be substantially evenly distributed on the second wall. Advantageously, this ensures that air is uniformly circulated around the vapour generating chamber.

The second passageway may be arranged to prevent solid vapour generating material from passing from the vapour generating chamber through the second passageway whilst allowing generated vapour to pass through the second opening.

The second passageway may have any suitable shape which allows vapour to leave the vapour generating chamber. For example, in some embodiments the second passageway may comprise a plurality of small substantially circular openings or a plurality of substantially polygonal shaped openings such as rectangles. The plurality of openings may be arranged in an annular arrangement. The plurality of openings may be substantially evenly spaced apart. In other embodiments the opening may be a single opening having an annular shape.

The vapour generating chamber may be arranged to be removable from the vapour generating device. This allows a user to remove the vapour generating chamber, when the vapour generating device is not in use, for cleaning.

The vapour generating device may further comprise an outer chamber arranged to receive the vapour generating chamber. The outer chamber may comprise a third passageway substantially opposite at least the first or the second passageway.

The outer chamber may comprise a third wall substantially opposite the second wall of the vapour generating chamber. The third wall and the second wall may create a gap therebetween. The third passageway may be defined within a wall of the outer chamber. The third passageway may be defined within the third wall of the outer chamber.

The second passageway and the third passageway may be spaced apart from each other by a gap. This allows air to flow easily between the second and third passageways, providing an unobstructed air flow passage between the vapour generating chamber and the air outlet.

The vapour generating device may further comprise a heater arranged to heat solid vapour generating material contained in the vapour generating chamber. The heater may be external to the vapour generating chamber. The vapour generating device may further comprise a controller arranged to instruct the heater to heat the vapour generating material in-between detection of puffs by a detector. Activating the heater between puffs, or usage, helps ensure that the vapour generating material is maintained at an optimum temperature while the vapour generating device is turned on.

The solid vapour generating material may be any suitable material capable of forming a vapour. The material may be a semi-solid material. The material may comprise plant derived material and in particular, the material may comprise tobacco. Typically, the solid vapour generating material is a solid or semi-solid tobacco substance. Examples of solid vapour generating materials include powder, granules, pellets, shreds, strands, porous material, foam, or sheets.

Preferably, the solid vapour generating material may comprise an aerosol-former. Examples of aerosol-formers include polyhydric alcohols and mixtures thereof such as glycerine or propylene glycol. Typically, the solid vapour generating material may comprise an aerosol-former content of between approximately 5% and approximately 50% on a dry weight basis. Preferably, the solid vapour generating material may comprise an aerosol-former content of approximately 15% on a dry weight basis.

The vapour generating material may be formed substantially in the shape of a stick which may have a mouthpiece filter. In this case the main body of the vapour generating material may be enclosed by a material. The material may be a sheet, such as paper, wrapped around the vaporisable material.

In some embodiments, the solid vapour generating material may be formed from a porous material (for example ceramic or cotton wool) which holds a liquid vapour material containing the aerosol-former. In other embodiments, a container may be provided which stores the liquid vapour material. The walls of the container may include liquid impermeable/vapour permeable portions. These liquid impermeable/vapour permeable portions may be equally spaced apart around a perimeter of the container.

The vapour generating material may include at least one of tobacco, humectant, glycerine, and propylene glycol. However, any other volatile material could be used from which a vapour or aerosol can be generated.

The lateral wall, or side wall, of the vapour generating chamber may have a base which is substantially opposite a second wall of the vapour generating chamber. The first passageway of the vapour generating chamber may surround the base of the lateral wall. That is, in some embodiments, the first passageway of the vapour generating device may extend along an edge between the lateral wall and the closure of the vapour generating device. This configuration also provides uniform air flow across the vapour generating chamber.

The closure may be pivotally attached to the vapour generating device. This may provide a simple mechanism for opening and closing the vapour generating chamber. Additionally, by attaching the closure to the vapour generating device, this ensures that the closure cannot become separated from the vapour generating device. This greatly reduces the chance of a user losing the closure, when they are placing the vapour generating substance inside the vapour generating chamber. This is important since the device will not work unless the vapour generating chamber is sealed. Furthermore, a pivotal attachment provides a quick and simple mechanism for opening the chamber within the device, which advantageously can be operated using only one hand if necessary.

The heater may be arranged external to the vapour generating chamber. That is to say, the heater is outside of the vapour generating chamber rather than inside the vapour generating chamber. The heater may be arranged to substantially surround the vapour generating chamber. The heater may comprise heating elements. Thus, the heating elements may be arranged outside of the vapour generating chamber such that the heating elements surround the vapour generating chamber. This ensures that the walls of the vapour generating chamber are being heated evenly. This helps provide a more consistent temperature within the vapour generating chamber which can reduce the chance of cold spots developing inside the vapour generating chamber.

The vapour generating device may be a hand-held device. The vapour generating device may be an electronic cigarette.

According to another aspect of the present invention there is provided a system comprising a vapour generating device as substantially described above and a solid vapour generating material.

BRIEF DESCRIPTION OF THE DRAWINGS

Embodiments of the present invention will now be described, by way of example only, with reference to the accompanying drawings in which.

SPECIFIC DESCRIPTION

Figure 1:
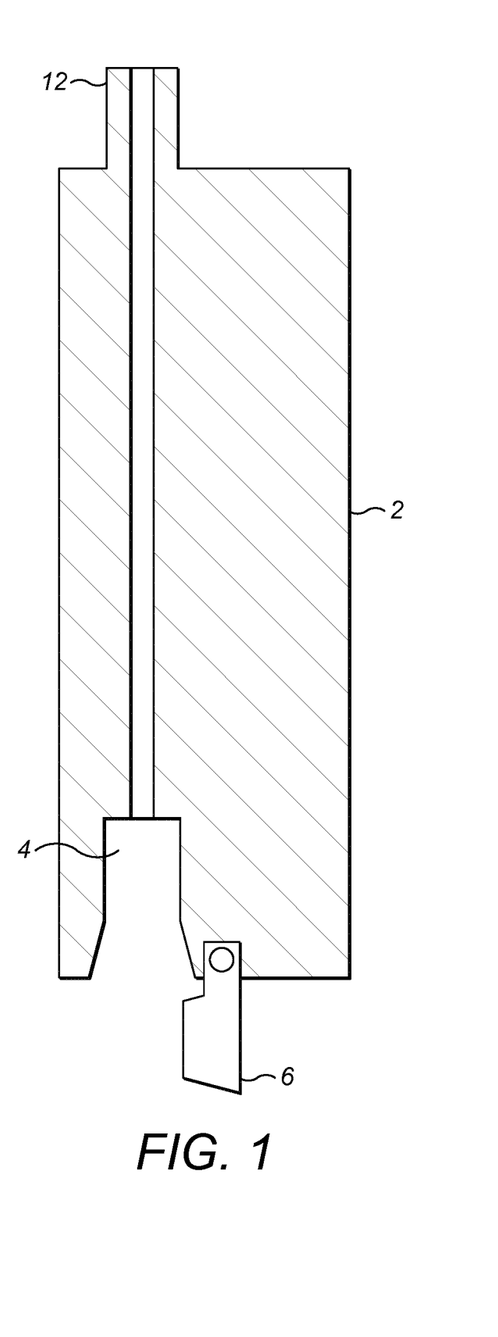
FIG. 1 is a schematic view of a vapour generating device comprising a closure, the closure in an open position.
Figure 2:
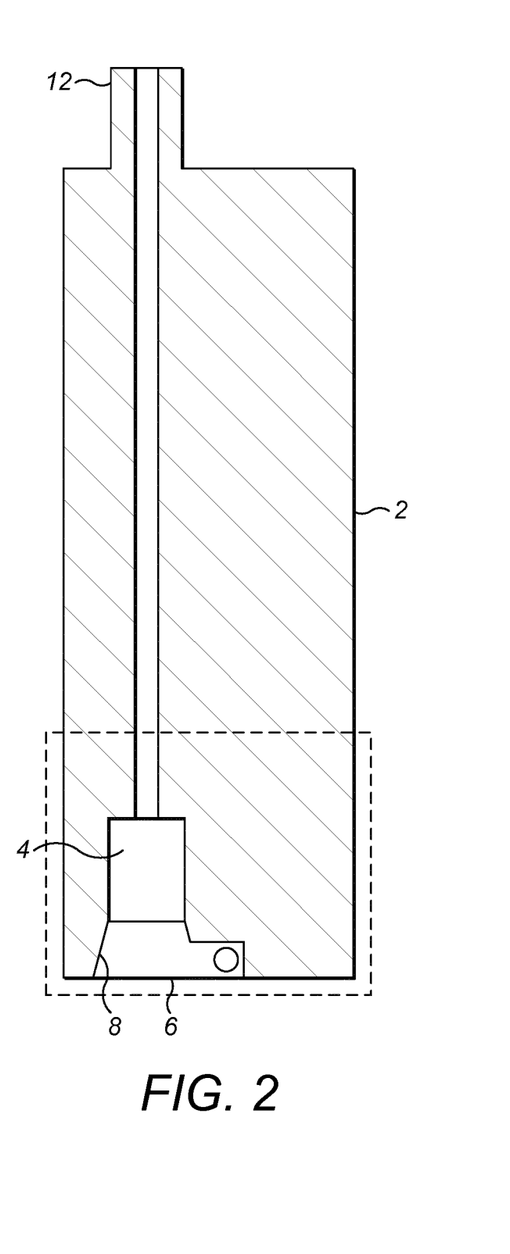
FIG. 2 is a schematic view of a vapour generating device comprising a closure, the closure in a closed position.

A vapour generating device 2, according to the invention, is shown generally in FIG. 1. The vapour generating device 2 includes a vapour generating chamber 4 for receiving solid vapour generating material and a closure 6 for retaining the vapour generating material inside the vapour generating chamber 4. When the closure 6 is in the closed position, as illustrated in FIG. 2, an air flow passageway 8 is defined which allows air to enter the vapour generating chamber 4. The air flow passageway 8 has an air inlet at one end, extending through the exterior of the vapour generating device and a first passageway or opening at the other end, extending into the vapour generating chamber 4. The vapour generating device 2 further includes a mouthpiece 12 in fluid communication with the vapour generating chamber 4. A heater heats the solid vapour generating material inside the vapour generating chamber 4, generating a vapour which is inhaled by a user via the mouthpiece 12.

Figure 3:
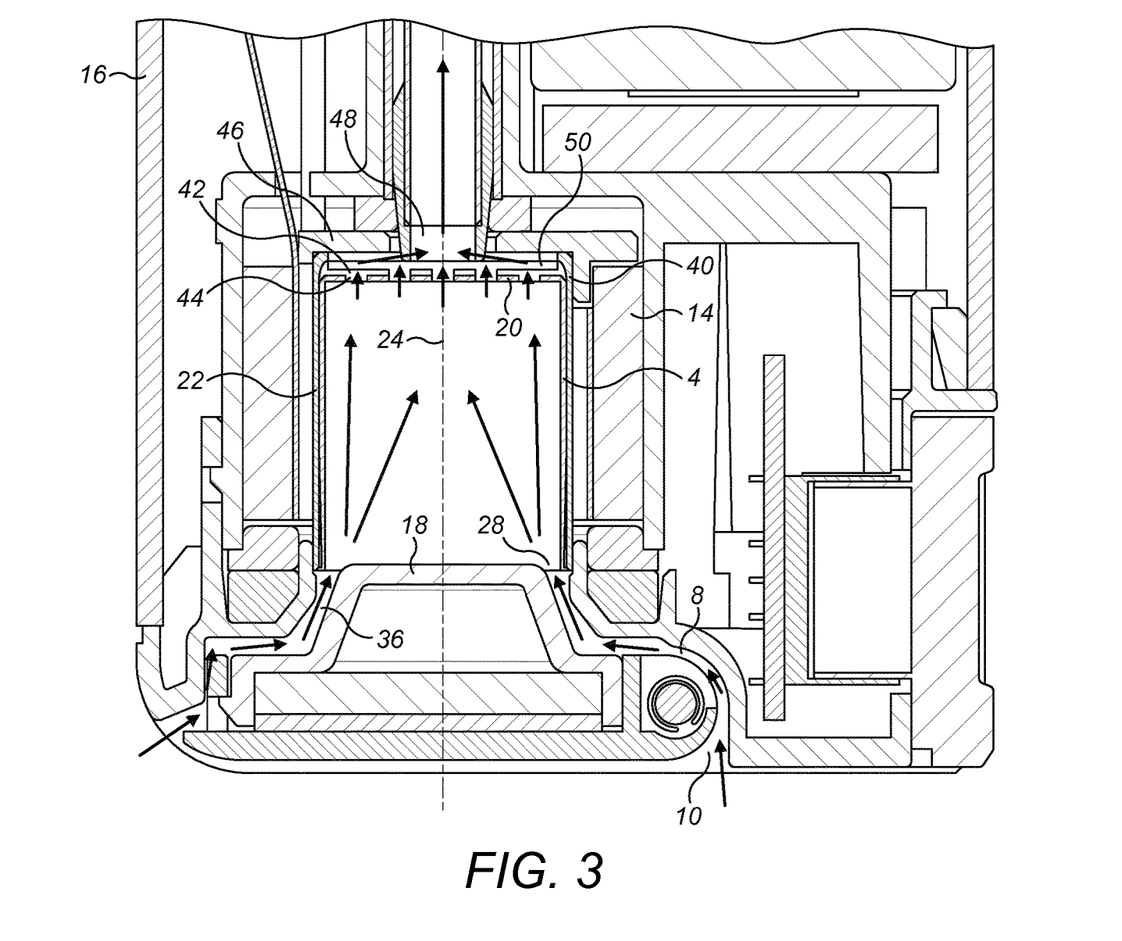
FIG. 3 is a cross-sectional view of a vapour generating device comprising a vapour generating chamber and a closure, the closure defining an opening.

Turning to FIG. 3, the structure of the vapour generating chamber 4 and closure 6 is shown in more detail. As can be seen in the figure, the vapour generating device 2 for heating vapour generating material (for example, tobacco) includes a vapour generating chamber 4, in the form of an oven, having heating elements 14 which surround the vapour generating chamber 4 and are insulated from the edges 16 of the vapour generating device 2.

The chamber 4 has a tubular form (for example a cylinder or prism) having a first end wall 18 forming a chamber base and a second end wall 20, opposite the first end wall 18, forming a chamber ceiling. One or more lateral walls 22 form the side (if the chamber is cylindrical in shape) or sides (if the chamber is a polygonal prism).

The vapour generating chamber 4 is contained within an outer chamber 40 which surrounds the lateral walls and ceiling of the vapour generating chamber 4. The heating elements surround the outer chamber 40, as well as the vapour generating chamber 4 as shown in FIG. 3.

The first end wall 18 of the chamber forms part of the closure 6, which is pivotally attached to the vapour generating device. The closure can be pivoted between an open position and a closed position. In the open position, the tubular chamber has an open end allowing the user to insert vapour generating material into the chamber 4. In the closed position, the chamber is a closed tube, the first end wall 18 acting as a lid to the chamber preventing vapour generating material from falling out of the chamber 4.

As well as allowing the user to insert vapour generating material into the vapour generating chamber 4, the closure 6 allows the user to remove the vapour generating chamber 4 from the vapour generating device 2 during cleaning. To remove the vapour generating chamber 4, the user slides the vapour generating chamber 4 out of the outer chamber 40. To insert the chamber 4, the user slides the chamber 4 into the outer chamber 40 until the second wall 20 of the vapour generating chamber 4 abuts a wall of the outer chamber 40.

The air inlet or inlets 10 are formed in an outer surface of the vapour generating device. The air inlets 10 are located at one end of the vapour generating device 2, typically at the base of the vapour generating device 2. As is shown in FIG. 3, one air inlet 10 is located in a corner of the vapour generating device 2, where the base of the vapour generating device 2 meets a sidewall of the vapour generating device 2. Another air inlet 10 is located within the base of the vapour generating device 2, spaced apart from the first air inlet 10.

As mentioned, the air inlets 10 are connected to the vapour generating chamber 4 via the air flow passageway 8. The air flow passageway 8 therefore provides a fluid communication path between the air inlets 10 and the vapour generating chamber 4.

The vapour generating chamber 4 has a longitudinal axis 24 which is perpendicular to the plane of the first 18 and second 20 end walls of the vapour generating chamber 4. The air flow passageway 8 is arranged so that air that is drawn into the vapour generating device 2 through the air inlets 10 is directed towards the longitudinal axis 24 of the vapour generating chamber 4. By directing the air flow into the centre of the vapour generating chamber 4 rather than, for example, to the sides a more uniform air flow throughout the vapour generating chamber 4 is achieved.

When the closure 6 is in the closed position an opening or openings 28 are defined within the vapour generating chamber 4. This is because when the closure 6 is in the closed position, a gap 36 is formed between the lateral walls 22 of the vapour generating chamber 4 and the first end wall 18, or closure 6. This gap 36 defines the opening 28 in the vapour generating chamber 4. The openings 28 form the first passageway 28.

The first opening or openings 28 in the vapour generating chamber 4 are located at the base of the vapour generating chamber 4 where the first end wall 18 of the vapour generating chamber 4 meets the lateral walls 22 of the vapour generating chamber 4. The openings 28 are therefore located at the edges of the first end wall of the vapour generating chamber 4. As the first end wall 18 of the vapour generating chamber 4 forms part of the closure 6, the openings 28 may also be thought of as being located at the edges of a part of the closure 6 where the closure 6 meets the lateral walls 22 of the vapour generating chamber 4.

The second wall of the vapour generating chamber 4 includes a second opening 42. The second opening 42 is defined by a plurality of evenly spaced apart holes 44 within the surface area of the second wall 20 of the vapour generating chamber 4. The second opening 42 is in fluid communication with the mouthpiece 12 allowing the user to inhale the vapour generated in the vapour generating chamber 4.

By configuring the second opening 42 as a plurality of small holes 44, the vapour generating material inside the vapour generating chamber 4 is prevented from passing through the second opening 42. This is because the holes 44 are smaller than the particles making up the solid vapour generating material. Although the material is prevented from passing through the second opening 42, the holes 44 are sized so that the vapour that is generated within the chamber 4 is able to pass through the second wall 20 and out through the mouthpiece 12.

As mentioned previously, the outer chamber 40 surrounds the vapour generating chamber 4. The outer chamber 40 therefore has a similar shape to the vapour generating chamber 4 and includes a third wall 46, forming a ceiling portion of the outer chamber 40, and side walls. The third wall 46 includes a third opening 48, positioned centrally within the third wall 46 as shown in FIG. 3. The third opening 48 is in fluid communication with both the second opening 42 and the mouth piece 12. Vapour is therefore able to flow from the vapour generating chamber 4, through the second opening 42, through the third opening 48, and out through the mouthpiece 12.

In order to allow the vapour to flow between the second opening 42 and the third opening 48, the second wall 20 of the vapour generating chamber 4 and the third wall 46 of the outer chamber 40 are axially spaced apart from each other. This means that when the vapour generating chamber 4 is fully inserted into the outer chamber 40 a gap 50 is created between the second 20 and third walls 46.

Figure 4:
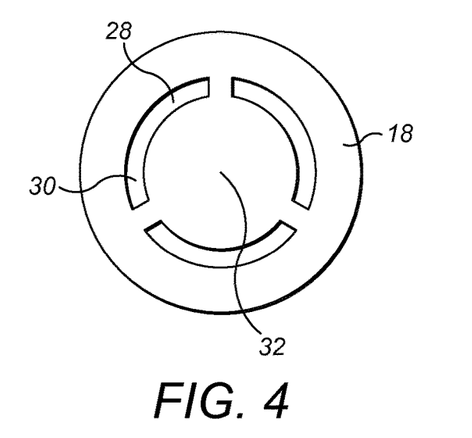
FIG. 4 is an end view of a first example of a closure defining an opening.

The structure of the first opening 28 can be more clearly see in FIGS. 4-7. Looking first at FIG. 4, a first example of an opening 28 is shown. In this example the opening 28 is located within the first end wall 18 of the vapour generating chamber 4. As can be seen in FIG. 4, the opening 28 is made up of three arcs 30 spaced apart from each other, the three arcs 30 being positioned so that the opening 28 has an annular shape. The annular opening 28 surrounds the central part 32 of the first end wall 18 of the vapour generating chamber 4. In some examples the annular opening 28 surrounds more than 50% of the total surface area of the first end wall 18 of the vapour generating chamber 4. As the first end wall 18 of the vapour generating chamber 4 is part of the closure 6, the annular opening 28 surrounds a central part of the closure 6.

Figure 5:
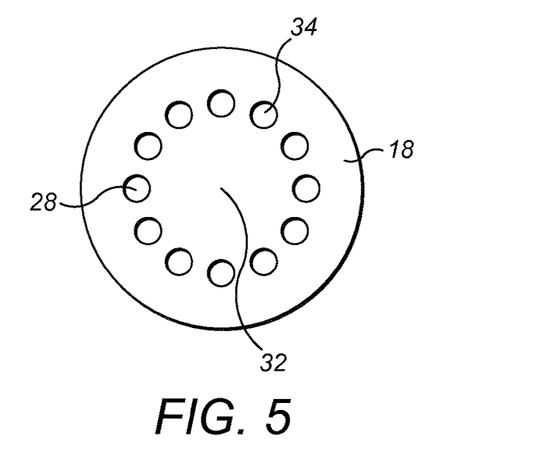
FIG. 5 is an end view of a second example of a closure defining an opening.

In other examples, the first opening 28 is made up of a plurality of small holes 34, as can be seen in FIG. 5. The holes 34 are circular in shape and equally spaced apart from each in an annular arrangement. Again, the opening 28 defined by the annular arrangement of holes 34 surrounds the central part 32 of the first end wall 18 of the vapour generating chamber 4. As before, the opening 28 formed by the plurality of holes 34 surrounds more than 50% of the total surface area of the first end wall 18 of the vapour generating chamber 4. The plurality of holes 34 therefore surrounds a central part of the closure 6.

Figure 5A:
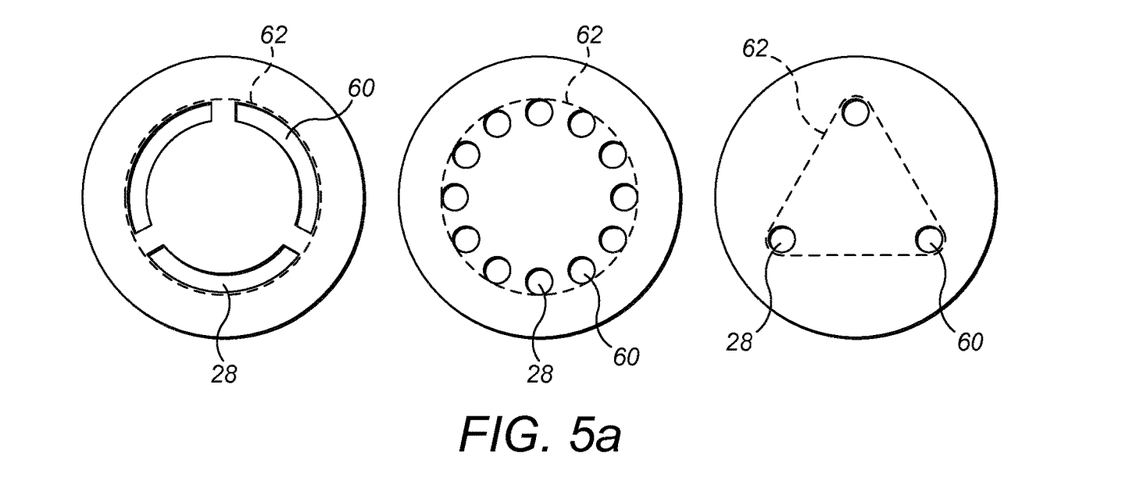
FIG. 5a is an end view of a closure illustrating the relationship between the openings and the area of the closure.
Figure 6:
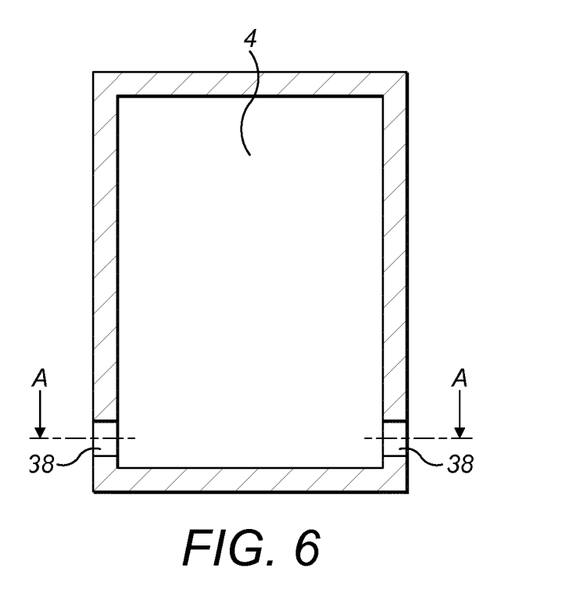
FIG. 6 is a side view of third example of a closure defining an opening.

In this context, the area that is surrounded by the opening 28 can be considered to be an area defined by a virtual rope or perimeter, the path of the virtual rope or perimeter being defined by the position of the openings. The openings 28 can be thought of as representing posts 60, such as fence posts. It would then be possible to wrap a virtual rope 62 around the posts 60 so that a perimeter is defined. The shape of the perimeter depends on the configuration of the openings. For example, a large number of openings in an annular arrangement would form a substantially circular path. This can be seen in the middle illustration in FIG. 5*a*. A small number of openings would form a polygon, as shown in the right most illustration in FIG. 5*a*. The area surrounded by the path defined by the virtual rope or perimeter is the area that is surrounded by the openings 28.

Figure 7:
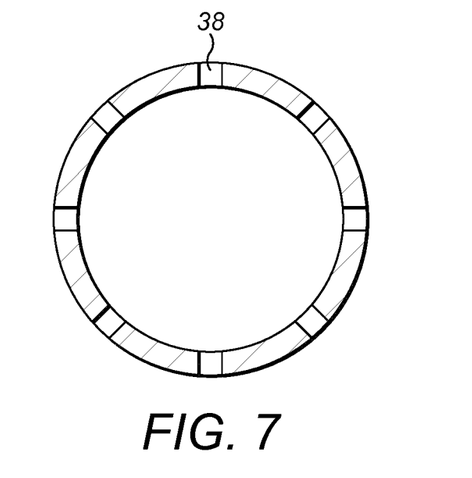
FIG. 7 is a cross-sectional view of a closure along the line A-A in FIG. 6.

In other examples, instead of the first opening 28 being defined within the first end wall 18 of the vapour generating chamber 4 and surrounding a central part of the first end wall 18, the opening 28 is defined within the lateral walls 22 of the vapour generating chamber 4. This configuration can be seen in FIG. 6 which shows two openings 28, one in each lateral wall 22 of the vapour generating chamber 4. This configuration is similar to the arrangement shown in FIG. 5 in that the opening 28 is defined by a plurality of spaced apart holes 38 in the lateral wall 22 of the vapour generating chamber 4. As can be seen in FIG. 7, the plurality of holes 38 are equally spaced apart around the perimeter of the vapour generating chamber 4, i.e arranged to surround the vapour generating chamber, at the base of the side lateral wall 22.

In use, the user inhales the vapour by drawing air into the device 2 from the air inlets 10, through the vapour generating chamber 4 containing the vapour generating material, and out of the mouthpiece 12 via the series of openings. The vapour is generated by heating the vapour generating material using the surrounding heaters. Heating via the heaters is controlled by a controller present in the vapour generating device 2. The controller sends signals to the heater, turning it on and off, to ensure that the vapour generating material is heated to an optimum temperature.

The vapour generating device 2 also includes a detector which detects when the user is using the device. The detector detects when the user is drawing air into the device, known as puff detection. As well as heating the vapour generating material during usage, the controller instructs the heater to heat the vapour generating material in between puffs detected by the detector. In other words, the control activates the heater during use and in between puffs. This helps keep the vapour generating material at the optimum temperature for generating the vapour.

Figure 8:
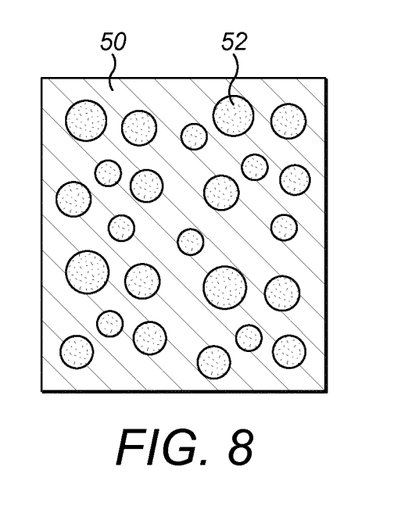
FIG. 8 is a schematic view of an example of vapour generating material.
Figure 9:
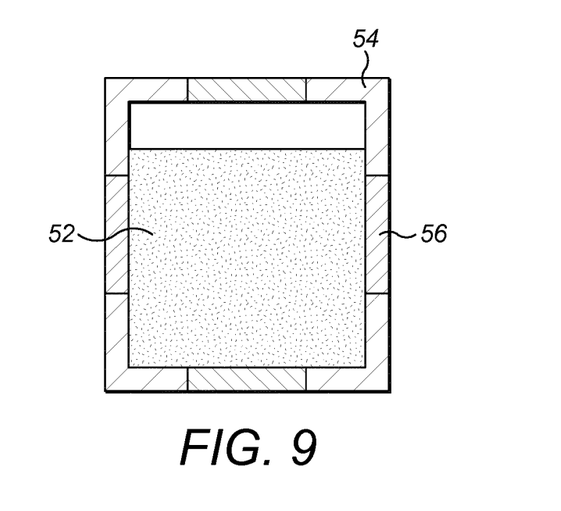
FIG. 9 is a schematic view of another example of vapour generating material.

Examples of solid vapour generating material for use with the vapour generating device are illustrated in FIGS. 8 and 9. In some examples, the solid vapour generating material is formed from a porous material 50 (for example ceramic or cotton wool) which holds a liquid vapour material 52, as shown in FIG. 8. In other examples, a container 54 is provided which stores the liquid vapour material 52. The walls of the container 54 include liquid impermeable/vapour permeable portions 56 equally spaced apart around the perimeter of the container 54, as shown in FIG. 9.

As the skilled person will appreciate, the vapour generating device described herein allows air to flow uniformly around the vapour generating chamber whilst keeping the structure of the vapour generating device simple, ensuring it can be operated easily by a user and reducing its manufacturing complexity.

The invention claimed is:

1. A vapour generating device arranged to receive solid vapour generating material, the device comprising:
    a vapour generating chamber arranged to contain the solid vapour generating material;
    a closure arranged to seal the vapour generating chamber; and
    a first passageway arranged between the exterior of the vapour generating device and the vapour generating chamber, such that the passageway allows air to enter the vapour generating chamber;
    wherein
    the vapour generating chamber comprises a side wall arranged to define the first passageway between the closure and the side wall.

2. The vapour generating device according to claim 1 wherein the closure is arranged to define the first passageway of the vapour generating device when the closure is in a closed position.

3. The vapour generating device according to claim 1 wherein the first passageway comprises an annular opening.

4. The vapour generating device according to claim 1 wherein the first passageway comprises a plurality of openings.

5. The vapour generating device according to claim 1 wherein at least 50% of the total surface area of the first wall of the closure is surrounded by the first passageway.

6. The vapour generating device according to claim 1 wherein the first passageway comprises a plurality of gaps between the closure and the side wall.

7. The vapour generating device according to claim 1 wherein the first passageway is arranged such that air that enters the vapour generating chamber is directed towards a central axis of the vapour generating chamber.

8. The vapour generating device according to claim 1 wherein the vapour generating chamber comprises a second passageway substantially opposite the first passageway between an interior of the vapour generating chamber and an air outlet such that the second passageway allows air to exit the vapour generating chamber.

9. The vapour generating device according to claim 8 wherein the vapour generating chamber comprises a second wall substantially opposite the first wall and the second passageway is substantially evenly distributed on the second wall.

10. The vapour generating device according to claim 8 wherein the second passageway is arranged to prevent the solid vapour generating material from passing from the vapour generating chamber through the second passageway whilst allowing generated vapour to pass through the second passageway.

11. The vapour generating device according to claim 1 wherein the vapour generating chamber is arranged to be removable from the vapour generating device.

12. The vapour generating device according to claim 9 further comprising an outer chamber arranged to receive the vapour generating chamber.

13. The vapour generating device according to claim 12 wherein the outer chamber comprises a third wall substantially opposite the second wall of the vapour generating chamber and wherein the third wall and the second wall create a gap therebetween.

14. The vapour generating device according to claim 12 wherein the outer chamber comprises a third passageway substantially opposite at least the first or the second passageway.

15. The vapour generating device according to claim 1 further comprising a heater arranged to heat the solid vapour generating material contained in the vapour generating chamber.

16. The vapour generating device according to claim 1 wherein the closure is pivotally attached to the vapour generating device.

17. The vapour generating device according to claim 15 wherein the heater is arranged external to the vapour generating chamber.

18. The vapour generating device according to claim 15 wherein the heater is arranged to substantially surround the vapour generating chamber.

19. A system comprising the vapour generating device according to claim 1 and the solid vapour generating material.

20. A vapour generating device arranged to receive solid vapour generating material, the device comprising:
    a vapour generating chamber arranged to contain the solid vapour generating material;
    a closure arranged to seal the vapour generating chamber; and
    a first passageway arranged between the exterior of the vapour generating device and the vapour generating chamber, such that the passageway allows air to enter the vapour generating chamber;
    wherein:
    the vapour generating chamber comprises a first wall and the first passageway is arranged to extend through the first wall and surround at least part of the first wall; or
    the vapour generating chamber comprises a side wall arranged to define the first passageway between the closure and the sidewall; or
    the vapour generating chamber comprises a side wall and the first passageway is arranged to surround the vapour generating chamber at a base of the sidewall, and wherein the first passageway comprises a plurality of gaps between the closure and the side wall.

* * * * *